(12) United States Patent
Van Der Zaag et al.

(10) Patent No.: US 10,619,202 B2
(45) Date of Patent: Apr. 14, 2020

(54) OPTICAL CONTROLLING OF A CHEMICAL REACTION

(71) Applicant: KONINKLIJKE PHILIPS N.V., Eindhoven (NL)

(72) Inventors: Pieter Jan Van Der Zaag, Waalre (NL); Anke Pierik, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 731 days.

(21) Appl. No.: 15/038,752

(22) PCT Filed: Nov. 20, 2014

(86) PCT No.: PCT/EP2014/075067
§ 371 (c)(1),
(2) Date: May 24, 2016

(87) PCT Pub. No.: WO2015/078755
PCT Pub. Date: Jun. 4, 2015

(65) Prior Publication Data
US 2017/0037468 A1  Feb. 9, 2017

(30) Foreign Application Priority Data

Nov. 29, 2013 (EP) ..................................... 13194975

(51) Int. Cl.
*C12Q 1/6874* (2018.01)
*G01N 21/64* (2006.01)
*B01J 19/00* (2006.01)

(52) U.S. Cl.
CPC ........ *C12Q 1/6874* (2013.01); *B01J 19/0046* (2013.01); *G01N 21/648* (2013.01);
(Continued)

(58) Field of Classification Search
CPC .... B01D 53/007; B01D 51/10; B01D 53/885; B01D 2259/4508; B01D 2257/708;
(Continued)

(56) References Cited

U.S. PATENT DOCUMENTS 9,103,785 B2    8/2015  Okura
9,823,196 B2 *  11/2017 Wimberger-Friedl .......................
                                    C12Q 1/6874
(Continued)

FOREIGN PATENT DOCUMENTS

CN    101831384    9/2010
WO    00/53805     9/2000
(Continued)

OTHER PUBLICATIONS

Metzker, "Sequencing technologies, the next generation", Nature Review Genetics 11 (2010) 31-46.
(Continued)

*Primary Examiner* — Nicholas A Smith
*Assistant Examiner* — Colleen M Raphael

(57) ABSTRACT

A device (100) and a method optically control a chemical reaction in a reaction chamber (149) holding a reagent fluid (114). The chemical reaction includes a nucleic acid sequencing on a wiregrid. Based on strong optical confinement of excitation light (110) and of cleavage light (112), the sequencing reaction can be read-out. Stepwise sequencing is achieved by using nucleotides with optically cleavable blocking moieties. After read-out the built in nucleotide is deblocked by cleavage light through the same substrate. This ensures that only bound nucleotides will be unblocked. In order to avoid overheating by cleavage light, the reagent fluid is circulated along the surface of the substrate (101).

19 Claims, 2 Drawing Sheets

(52) U.S. Cl.
CPC ..... *G01N 21/6428* (2013.01); *G01N 21/6452* (2013.01); *B01J 2219/0059* (2013.01); *B01J 2219/00286* (2013.01); *B01J 2219/00454* (2013.01); *B01J 2219/00495* (2013.01); *B01J 2219/00585* (2013.01); *B01J 2219/00596* (2013.01); *B01J 2219/00711* (2013.01); *G01N 2021/6439* (2013.01); *G01N 2201/061* (2013.01)

(58) Field of Classification Search
CPC ........ B01D 2255/802; B01D 2259/804; B01D 2257/91; F24F 3/166; F24F 2003/1667; F24F 2003/1628; A61L 9/205; C12Q 1/6874; G01N 21/6428; G01N 21/648; G01N 2201/061; G01N 2021/6439; G01N 21/6452; B01J 19/0046; B01J 2219/00596; B01J 2219/00711; B01J 2219/0059; B01J 2219/00585; B01J 2219/00454; B01J 2219/00495; B01J 2219/00286
USPC .................. 204/157.15, 157.68; 422/186
See application file for complete search history.

(56) References Cited

U.S. PATENT DOCUMENTS

| | | | |
|---|---|---|---|
| 2002/0058329 A1* | 5/2002 | Singh | B01J 19/0046 435/287.2 |
| 2003/0032204 A1* | 2/2003 | Walt | G21K 1/006 436/518 |
| 2006/0257878 A1* | 11/2006 | Hagiwara | B01L 3/5027 435/6.12 |
| 2010/0285490 A1* | 11/2010 | Dees | G01N 33/54373 435/7.1 |
| 2011/0311963 A1* | 12/2011 | Lafferty | C12Q 1/6874 435/6.1 |
| 2012/0009663 A1 | 1/2012 | Enzelberger | |
| 2015/0299784 A1* | 10/2015 | Fan | C12Q 1/6874 506/4 |

FOREIGN PATENT DOCUMENTS

| | | |
|---|---|---|
| WO | 2006/071631 | 7/2006 |
| WO | 2007/072418 | 6/2007 |
| WO | 2007/123744 | 11/2007 |
| WO | 2009158451 | 12/2009 |
| WO | 2011/116120 | 9/2011 |
| WO | 2013/105025 | 7/2013 |

OTHER PUBLICATIONS

Fuller, et al., "The challenges of sequencing by synthesis", Nature Biotechnology, vol. 27, No. 11, Nov. 1, 2009.

Litosch et al., Improved nucleotide selectivity and termination of 30-OH unblocked reversible terminators by molecular tuning of 2-nitrobenzyl alkylated HOMedU triphosphates, Nucleic Acids Research, 2011, vol. 39, No. 6 e39.

* cited by examiner

OPTICAL CONTROLLING OF A CHEMICAL REACTION

CROSS REFERENCE TO RELATED APPLICATIONS

This application is the U.S. National Phase application under 35 U.S.C. § 371 of International Application No. PCT/EP2014/075067, filed Nov. 20, 2014, published as WO 2015/078755 on Jun. 4, 2015, which claims the benefit of European Patent Application Number 13194975.2 filed Nov. 29, 2013. These applications are hereby incorporated by reference herein.

FIELD OF THE INVENTION

The present invention relates to a device and a method for optically controlling a chemical reaction in a reaction chamber comprising a reagent fluid. In particular, the present invention relates to a device for optically controlling an iterative stepwise reaction to determine a sequence of a nucleic acid, and a method for optically controlling an iterative stepwise reaction to determine a sequence of nucleic acid.

BACKGROUND OF THE INVENTION

The WO 2013/105025 A1, which is incorporated into the present text by reference, describes a device and a method for optically controlling the iterative incorporation of fluorescently labeled nucleic acids into a molecule attached to the surface of a wiregrid substrate. Based on a strong optical confinement of excitation light and of cleavage light by evanescent waves, the sequencing reaction can be read-out without washing the surface. Stepwise sequencing is achieved by using nucleotides with optically cleavable blocking moieties. After read-out the built in nucleotide is deblocked by cleavage light through the same substrate. This ensures that only bound nucleotides will be unblocked.

SUMMARY OF THE INVENTION

It would be advantageous to have a procedure that allows for an optically controlled chemical reaction, particularly a nucleic sequencing reaction, with an increased throughput.

According to a first aspect, an embodiment of the invention relates to a device for optically controlling a chemical reaction in a reaction chamber, said chamber comprising a reagent fluid. The device comprises the following components:

A substrate for binding at least one molecule on a first surface of the substrate, wherein said first surface is a wall (border) of the reaction chamber. The substrate may particularly be a wiregrid.

An optical arrangement configured to direct light to the substrate to optically induce a photochemical cleavage reaction. Due to its effect, this light will be called "cleavage light" in the following.

A circulation arrangement for circulating the reagent fluid in the reaction chamber.

The "reaction chamber" is typically an open cavity, a closed cavity, or a cavity connected to other cavities by fluid connection channels.

According to a second aspect, an embodiment of the invention relates to a method for optically controlling a chemical reaction in a reaction chamber comprising a reagent fluid, said method comprising the following steps:

Providing a substrate with a molecule bound on a first surface of the substrate, wherein said first surface is a wall of the reaction chamber.

Irradiating the substrate with cleavage light of a cleavage wavelength $\lambda_{CL}$, preferably UV light, by an optical arrangement and thereby optically inducing a photochemical cleaving reaction.

Circulating the reagent fluid in the reaction chamber, preferably along the first surface of the substrate.

It shall be noted that all embodiments of the present invention concerning a method, might be carried out with the order of the steps as described, nevertheless this has not to be the only and essential order of the steps of the method. All different orders and combinations of the method steps are herewith described.

The described device and method are based on the same basic idea, i.e. the circulation of reagent fluid along a reaction surface that is irradiated with cleavage light. Explanations and embodiments described for the device are therefore analogously valid for the method, too, and vice versa.

The device and the method allow for (photo-) chemical reactions taking place with a high throughput at the surface of the substrate. This is because the circulation of reagent fluid along the surface guarantees that heat which is produced by the irradiation of cleavage light is carried away. Hence high intensities of cleavage light can be applied without damaging material at the surface, which enables higher reaction rates.

In the following various preferred embodiments will be described in more detail that can be realized both in combination with the device as well as with the method (even if they are only explained for one of the device and the method). Synergistic effects may arise from different combinations of the embodiments although they might not be described in detail.

Circulation of reagent fluid in the reaction chamber is preferably done such that (excess) heat is removed from the first surface. This may for example be achieved if reagent fluid in a volume immediately at and/or close to the first surface is exchanged (moved) due to the circulation. In particular, at least a part of the circulation may be oriented along the first surface of the substrate. Other patterns of circulation are however possible, too, for example with a fluid flow perpendicular to and/or away from the first surface.

Circulation of the reagent fluid may take place in a passive way, for example driven by gravity, convection and/or capillary forces. In a preferred embodiment, the reagent fluid is actively pumped. This can particularly be achieved by providing the circulation arrangement with a pumping element. Thus the timing and/or intensity of the reagent circulation can be controlled and adjusted by the user and/or by an automatic controller. Pumping may for example be controlled in a feedback loop based on a sensed temperature (e.g. of the reagent fluid) such that the temperature at the reaction surface is always kept below a given threshold.

In another embodiment, the reagent fluid may be cooled. The circulation arrangement may for example comprise a cooling element for this purpose. Cooling may for example be achieved by guiding the reagent fluid along a heat exchange surface through which excess heat can be transferred to a cooling medium (e.g. the surrounding atmosphere). Additionally or alternatively, means for actively cooling the reagent fluid may be provided, too, for example a Peltier element.

The circulation arrangement may preferably comprise at least one pneumatically driven actuator, for example a pneumatically driven pump. This allows for an easy integration of the device with a pneumatically operated (micro-) fluidic device.

In another embodiment, the circulation of the reagent fluid may be synchronized with the irradiation of cleavage light. In this context, the term "synchronization" shall refer to any coordinated timing of circulation on the one hand side and irradiation on the other hand side. In a particular case, circulation may take place simultaneously to the irradiation of cleavage light (optionally with some time shift and/or temporal lag).

It was already mentioned that the circulation of reagent fluid prevents overheating of the volume at the surface of the substrate. Accordingly, comparatively high intensities of the cleavage light can be applied. In a preferred embodiment, intensity of the cleavage light is larger than about 0.1 mW/cm$^2$, larger than about 0.5 mW/cm$^2$, larger than about 1 mW/cm$^2$, or larger than about 5 mW/cm$^2$.

In the following, further embodiments of the invention will be explained for which additional information may be found in the WO 2013/105025 A1.

In the context of the present invention, the term "blocking moiety" is to be understood as a moiety which blocks a synthesizing activity of an enzyme in the case where the blocking moiety is incorporated into a molecule at which the enzyme performs a synthesizing process. A blocking moiety may be e.g. a blocking molecule.

In the context of the present invention, the term "cleavable" should be understood as allowing to be cleaved away by absorbing cleavage light of wavelength $\lambda_{CL}$.

In the context of the present invention it should be understood, that every embodiment of the optical arrangement disclosed herein may be configured to emit polarized excitation light and polarized cleavage light. Thus, a polarizer or already polarized light sources may be used. Details will be described later on.

Furthermore, the term "excitation light" in the context of the present invention applies to the wavelength $\lambda_{Ex1}$, $\lambda_{Ex2}$, $\lambda_{Ex3}$ and $\lambda_{Ex4}$, respectively.

According to an exemplary embodiment of the invention, a device of the kind defined above for optically controlling a nucleic acid sequence is presented. In particular, the device is configured to optically control an iterative stepwise reaction to determine a sequence of a nucleic acid by synthesis. Alternatively, instead of sequencing by synthesis, a synthesis by ligation is also to be understood in the scope of the present invention. The presented device comprises a substrate for binding at least one molecule on a first surface of the substrate. The device further comprises an optical arrangement which is configured to direct excitation light of at least a first excitation wavelength $\lambda_{Ex1}$ to the substrate to excite a fluorescent label of a first nucleotide which is incorporated into the molecule that is bound on the first surface of the substrate. The optical arrangement is further configured to receive and detect fluorescent light emitted by the fluorescent label of the first nucleotide which is incorporated into the bound molecule. Furthermore, the optical arrangement is configured to direct cleavage light of a cleavage wavelength $\lambda_{CL}$, preferably UV light, to the substrate to optically induce a photochemical cleavage reaction at the first incorporated nucleotide to cleave a blocking moiety and the fluorescent label away from the first incorporated nucleotide. Furthermore, the substrate is configured to confine the excitation light and is configured to provide thus for an evanescent wave of the excitation light at the first surface of the substrate. Furthermore, the substrate is configured to confine the cleavage light, preferably UV light, and is further configured to provide for an evanescent wave of cleavage light at the first surface of the substrate. The device allows for ensemble based easy read out but no or a reduced number of washing steps are required any more, meaning a single reagent filling for all reads.

Stepwise sequencing is achieved by using nucleotides with optically cleavable blocking groups. After read-out, the built-in nucleotide is unblocked by cleavage light like for example UV radiation through the same nano-photonic substrate. This ensures that only bound nucleotides will be unblocked.

As it will be explained in detail in the following, the optical arrangement may also be configured to direct excitation light of a first, and a second, and a third and a fourth excitation wavelength $\lambda_{Ex1}$, $\lambda_{Ex2}$, $\lambda_{Ex3}$ and $\lambda_{Ex4}$, to the substrate to excite a fluorescent label of a first nucleotide incorporated into a molecule bound on the first surface of the substrate. Thereby, it can be ensured that e.g. four different nucleotides, like for example Adenine (A) and Guanin (G) and Thymine (T) or Uracil (U) and Cytosine (C), can be distinguished, when the respective nucleotide uses a specific and differentiated fluorescent label. However, if desired, also only two or three of the four excitation wavelength $\lambda_{Ex1}$, $\lambda_{Ex2}$, $\lambda_{Ex3}$ and $\lambda_{Ex4}$ described above may be directed by the device towards the substrate to excite the molecule, i.e., the fluorescent label of a nucleotide which is incorporated in the bound molecule. Details about four color systems, in which four different fluorescent labels for the above described nucleotides A, G, C, and T or U are used, will be explained hereinafter in more detail with respect to the following FIGS. 1 and 2. The bound molecule might be a nucleic acid fragment and can be understood as the nucleic acid whose sequence of nucleotides is determined by the present invention and which can be DNA fragment, DNA, RNA, mRNA or any other nucleic acid.

Furthermore, a person skilled in the art of sequencing or DNA sequencing is aware of the fact that the wavelength $\lambda_{Ex1}$, $\lambda_{Ex2}$, $\lambda_{Ex3}$ and $\lambda_{Ex4}$ are chosen in combination with the four fluorescent labels used for, for example, nucleotides A, G, C, and T or U. In other words, the wavelengths are chosen such that the used fluorescent labels, can be optically excited by the respected excitation light. Furthermore, the wavelength $\lambda_{CL}$ is chosen such that the desired cleaving reaction of the used nucleotides can be optically caused by irradiating said cleavage light.

It shall be noted that the molecule which is bound at the first surface of the substrate may for example be a DNA fragment, DNA, RNA, mRNA or another nucleic acid. Furthermore, also an enzyme, which will be described herein later on, may be bound to the first surface of the substrate. In the context of the present invention, the term "bound" shall be understood as a state in which the element is immobilized to the first surface of the substrate.

In addition, the substrate provides for spots which may be covered with clones of identical molecules, in order to increase the optical signal, which is received by detecting the fluorescence. Therefore, a substrate may be provided as an array of such spots with respectively different clones, such that throughput of sequencing is increased.

The evanescent wave of cleavage light and the evanescent wave of excitation light can be generated by the substrate of the presented device by providing for a wiregrid. This may allow for using a focused beam of high intensity such that the photo-optical reaction occurs at a high rate in a very limited area very close to the surface. The optical arrangement may comprise respective optical elements for the excitation and detection of fluorescence, i.e. the read-out, and respective optical elements for unblocking, i.e. activation, in a single optical arrangement unit or may also be comprised in physically differentiated elements.

Furthermore, the respective excitation light source may be comprised by the optical arrangement. Furthermore, the light source for emitting cleavage light may be comprised by the optical arrangement. Illumination for cleaving, i.e. unblocking and read-out, i.e. excitation and detection of fluorescence, can optionally occur though the same lens. However, if desired, also two different optical set-ups for unblocking and reading-out can be presented.

Furthermore the substrate may be out of a polymer e.g. poly-(cyclo-)olefin, poly-carbonate, polyester or PMMA. Also metal and semiconductors may be used.

According to another exemplary embodiment of the invention, the device further comprises the molecule which is bound to the first surface of the substrate. The device further comprises a solution ("reagent fluid") with a plurality of nucleotides and an enzyme. Therein, the nucleotides respectively comprise the blocking moiety. The blocking moiety is configured to block a synthesizing activity of the enzyme when the respective moiety is incorporated into the molecule bound to the first surface of the device.

If desired, the blocking moiety comprises the fluorescent label. However, the blocking moiety and the fluorescent label may be incorporated or positioned at the first nucleotide at different positions. They may be cleaved away in one single cleavage process or in different cleavage processes. This holds for every embodiment of the present invention.

As exemplary embodiments, the blocking moieties may be embodied as 3'-blocked reversible terminator or as 3'-unblocked reversible terminator as described and defined in "Sequencing technologies, the next generation" by Michael L. Metzker, *Nature Review Genetics* 11 (2010) 31-46. Therein, also termed "unblocked", said blocking moieties 3'-unblocked reversible terminator can be used as blocking an activity of an enzyme. Reversible terminators may be understood as ligands attached to the nucleotide/ribose unit which stops the incorporation of any subsequent nucleotide after the incorporation. They are reversible when upon cleavage by chemical or photochemical means this process can be undone and the polymerase can build in the next nucleotide. Furthermore, the 3'-blocked reversible terminator of Metzker et al. can be amended, for example chemically, to make them photo cleavable. Then, the photo cleavage with the cleavage light can be performed by means of the present invention. In addition, other complexes may be used as blocking moieties in combination with the respective enzyme as will be described later on. The skilled person knows which combination of enzyme and blocking moiety leads to the desired effect of blocking the synthesizing activity of the enzyme.

According to another exemplary embodiment, the substrate is configured as a wiregrid for the excitation light and for the cleavage light.

The wiregrid may comprise a pattern of metal wires on, for example, a glass substrate. The spacing between the wires acts as a metal-clad slab waveguide, in which the major contribution comes to two fundamental modes. For example, for TE polarized excitation light incident on the wires of the substrate of the present invention the resulting mode in between the wires is the evanescent mode, having an exemplary decay length of 16.8 nanometres for $\lambda=630$ nanometre. Therein assuming the wires of the substrate are filled with a medium having a refractive index of water, $n=1.33$. For TM polarized light, the resulting mode for a wiregrid is called a propagating mode, having a decay length of 1.2 µm in this example. For example, the wire height may be 60 nanometres in an example. Therein the TM polarized mode is transmitted with a loss of light in the order of 10% or less, while the TE polarized mode is evanescently decaying.

A different way to understand the wiregrid is to think of e.g. aluminium wires as metals which reflect excitation light with polarization parallel to the wires (TE polarization) and which transmit polarization orthogonal to the wires (TM polarization). The maximum transmission of TM polarized light may be higher than 95%. The evanescent field in the case of incident TE excitation light is depicted in both FIGS. 3a and 3b of WO 2013/105025 A1. The excitation light and the cleavage light irradiated by the optical arrangement of the present invention may be of such polarization in this and every other embodiment of the present invention.

The use of the wiregrid substrate of the presented device provides for an extreme optical confinement. In combination with a fast photochemical cleavage, which is used to decouple the so-called blocking moiety on the nucleotide to prevent continuation of the incorporation of the next nucleotide, the indicated advantages are realized. The use of the wiregrid has the additional advantage of being largely independent on the angle in incidence. Therefore, it can be used in combination with focused beams to achieve a high intensity locally while keeping the rest in the dark. In other words, the wiregrid allows to excite and be sensitive to only those molecules, for example DNA fragments, that are very close to the surface in the evanescent field and thus no detection or effect on any label nucleotide outside the evanescent field is caused. For example, the evanescent field may elongate about 20 nanometres from the first surface of the substrate. This may be the case for both the excitation light and the cleavage light.

A wiregrid substrate comprises a second surface opposite of the first surface and the optical arrangement is configured to irradiate the second surface of the substrate with the excitation light and the cleavage light. In other words, the substrates in the optical arrangement are positioned relative to each other such that the cleavage light and the excitation light are directly directed towards the second surface of the substrate. This may be seen as a backwards radiation of the substrate. On the front surface, the first surface, the regular wire structure is presented by the wiregrid. Between the regular metal wires, i.e. in the spaces between the wiregrid, the molecule, for example DNA fragments, is bound or immobilized.

The term "excitation light" in the context of the present invention applies to the wavelength $\lambda_{Ex1}$, $\lambda_{Ex2}$, $\lambda_{Ex3}$ and $\lambda_{Ex4}$, respectively. Consequently, for all four excitation wavelengths the substrate ensures that confinement and a creation of an evanescent wave of the respective light are generated. If desired, more or less light sources and/or fluorescent labels can be used without departing from the present invention.

According to another exemplary embodiment of the invention, the cleaving reaction takes a time $t_{cleavage}$, which depends on an intensity of the irradiated cleavage light. Furthermore, the incorporation of a second nucleotide into the bound molecule takes a time $t_{incorporation}$. The herein presented device comprises an optical arrangement which is configured and adjusted to provide the irradiated cleavage light with an intensity such that $t_{cleavage} < t_{incorporation}$.

Photo cleavage should only occur in those molecules which are incorporated already and bound to the surface. Reaction in the bulk would lead to unblocked reagents which could be built in without noticing and in this way introduce errors in the sequencing results. Therefore, it is valuable to only illuminate locally for a short period to make the cleavage reaction fast compared to the rate of incorporation of nucleotides by the enzyme. Working principle of the enzyme and the blocking moiety has been already described above. That disclosure applies within the herein described exemplary embodiment. The presented embodiments allow for synchronizing incorporation of the next nucleotides and ensure that the detected fluorescent signal is highly reliable.

The fact that the cleavage light is in an evanescent mode with respect to the substrate provides for the advantage that a repeated exposure does not lead to fluorescent labels in the solution which are bleached and which lose their function. In other words, the presented embodiment avoids such a bleaching and function-losing of fluorescent labels in solution.

For an improved synchronization of the incorporation of several nucleotides at several bound molecules, the unblocking step with the cleavage light should be carried out as fast as possible, i.e. with the highest cleavage light intensity possible. This may be achieved by focusing the cleavage light, preferably the UV light, with a lens and scanning the surface by moving the lens or the substrate. The unblocking step may be carried out after reading the sequencing step. This reading can be carried out by scanning a focus beam or step and scan with field illumination. It may also be possible to embody cleavage light as a single flash of, for example, UV light for the total surface. In view of the reaction rate for the base incorporation for the sequencing reaction, the local cleavage light illumination time should be, for example, below 1 minute.

BRIEF DESCRIPTION OF THE DRAWINGS

Exemplary embodiments of the invention will be described in the following drawings.

DETAILED DESCRIPTION OF EMBODIMENTS

Figure 1:
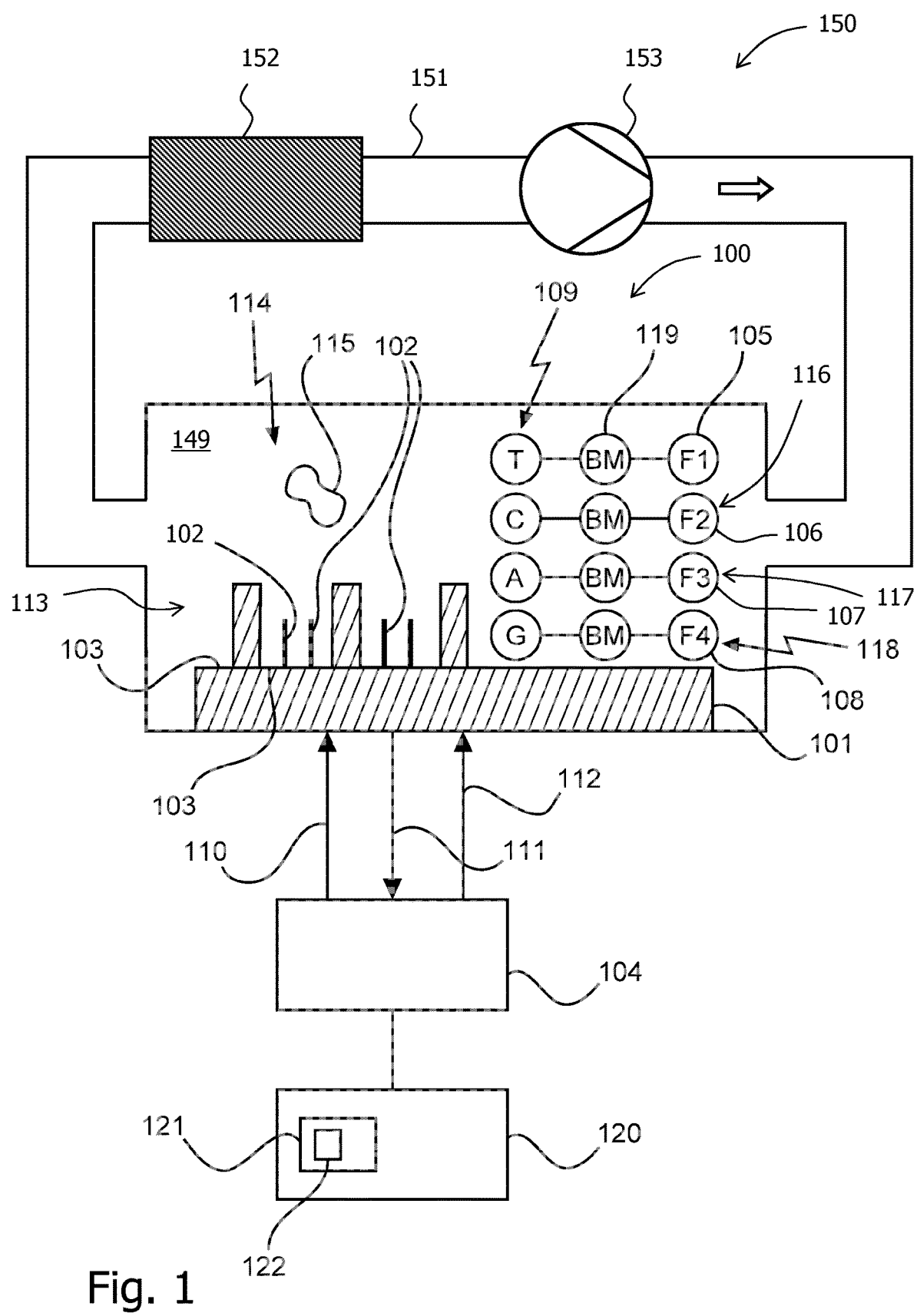
FIG. 1 schematically shows a first device according to an exemplary embodiment of the invention.

FIG. 1 depicts a device 100 for optically controlling a chemical reaction, in this case particularly an iterative stepwise reaction to determine a sequence of a nucleic acid by synthesis. The device comprises a substrate 101 for binding at least one molecule 102 on the first surface 103 of the substrate. The molecule 102 which is bound on the first or front surface 103 of the substrate 101 can for example be a fragment of a DNA. The first surface 103 constitutes a wall or border of a "reaction chamber" 149 in which a fluid to be processed (here a solution 114 that is described in more detail below) can be accommodated. The reaction chamber is typically a part of a larger (micro-) fluidic device or cartridge that is not shown in more detail.

Furthermore, the optical arrangement 104 is shown in FIG. 1. FIG. 1 schematically shows that the optical arrangement is configured to direct excitation light 110 of for example the first excitation wavelength $\lambda_{Ex1}$ to the substrate. Furthermore, four different nucleotides are schematically shown and are depicted with reference signs 109, 116, 117 and 118. For example, a first nucleotide 109 is shown as Thymine, T. The nucleotide 109 comprises a blocking moiety 119. Furthermore, the blocking moiety 119 comprises the first fluorescent label 105. In an analog way, the second nucleotide 116 is schematically depicted in FIG. 1, from which can be gathered that also a blocking moiety 119 and the second fluorescent label 106 are comprised. The third nucleotide 117 comprises also a blocking moiety and a third fluorescent label 107. Additionally, the fourth nucleotide 118 is schematically depicted which comprises also a blocking moiety and a fourth fluorescent label 108. However, sample 114 may comprise a much larger plurality of such nucleotides, and nucleotides 109, 116, 117 and 118 are shown here merely as a symbolic depiction.

Furthermore, FIG. 1 shows a solution 114 which fills the reaction chamber 149 and in which the nucleotides and the enzyme 115 are comprised. In case one of the shown four nucleotides is incorporated in the bound molecule 102, the presented device 100 provides for the following advantages. The optical arrangement is configured to receive and detect fluorescence light emitted by the fluorescent label of the first nucleotide incorporated into the bound molecule 102.

As can further be gathered from FIG. 1, the optical arrangement is configured to direct cleavage light 112 of cleavage wavelength $\lambda_{CL}$ to the substrate. This allows for optically inducing a photochemical cleavage reaction at the first incorporated nucleotide to cleave the respective fluorescence label from the first incorporated nucleotide. Furthermore, the substrate 101 is configured to confine excitation light such that an evanescent wave of the excitation light at the first surface of the substrate is created. Moreover, the substrate is configured to confine also the cleavage light such that an evanescent wave of the cleavage light at the first surface of the substrate is created.

In the embodiment of FIG. 1, the substrate 101 is configured as a wiregrid 113 for the excitation light 110 and for the cleavage light 112. Therefore, the wiregrid 113 comprises a regular pattern, like for example a regular metal wire structure. As can be gathered from FIG. 1, slit-like openings are provided between the regular patterns, in which openings the bound molecules 102 are immobilized at the first surface 103 of the substrate 101.

Furthermore, FIG. 1 depicts a processing unit 120 which comprises a computer-readable medium 121 on which a computer program element 122 is stored. Said program element 122 is adapted to instruct the processing unit 120 to further instruct the device 100 to perform the above and below described method for optically controlling an iterative stepwise reaction to determine a sequence of a nucleic acid by synthesis. The device 100 of FIG. 1 is configured to stepwise and optically induce the incorporation of nucleotides 109, 116, 117, 119 with a sequence, which corresponds to the sequence of nucleotides of the bound molecule 102. In case the molecule 102 is a DNA fragment, the nucleotides comprised by the sample 114 are incorporated into molecule 102 in a sequence that corresponds to the nucleotide sequence of molecule 102.

The device is further configured to base the determination of the sequence of the incorporated nucleotides on the received and detected response fluorescence light emitted by the fluorescent label of the respective incorporated nucleotide. Therefore, the presented device 100 of FIG. 1 firstly ensures that only nucleotides are read-out by the excitation light 110, which nucleotides are incorporated into a bound molecule 102 by the use of an evanescent wave of the excitation light. Secondly, the device 100 of FIG. 1 ensures that only bound nucleotides will be unblocked by the cleavage light which avoids a bleaching and loss of function of nucleotides that are not yet contained i.e. incorporated by the molecule 102. Consequently, the detected fluorescence signal 100 may be seen as the light 111, is highly reliable for the determination of the sequence of the nucleic acids.

Consequently, the cost and speed of the nucleic acid sequencing, like for example the DNA sequencing performed with the device 100 of FIG. 1 are both improved. Less reagents and enzymes are necessary as no washing step is needed. The device of FIG. 1 shows a simplification and cost reduction of sequencing. The presented device 100 of FIG. 1 allows for a new process combination by allowing an assemble-based easy read-out without any washing step, meaning a single reagent filling for all reads. The blocking moieties used within the exemplary nucleotides 109, 116, 117, 118 may for example be a photo-cleavable 3'-unblocked reversible terminator. However, also other blocking moieties, using for example steric hindering, may be used to reach the desired and above described effects.

Furthermore, the optical arrangement 104 as shown in FIG. 1 may be configured to provide the irradiated cleave light with an intensity such that the cleaving reaction time $t_{cleavage}$ is smaller than the time it takes to incorporate the second nucleotide into the molecule 102. As the cleaving reaction time $t_{cleavage}$ depends on the intensity of the irradiated cleavage light, FIG. 1 may provide for a selected combination of nucleotides with a specific blocking moiety and a configuration of the optical arrangement regarding the intensity of the cleavage light. In other words, the intensity of the cleavage light of the device of FIG. 1 is adapted such that for the used combination of nucleotides and blocking moieties the cleaving reaction time $t_{cleavage}$ is smaller than $t_{incorporation}$.

If desired, additionally or alternatively, the following set-up of device 100 may be provided to the user. If the reagent fluid is stationary and movement of molecules driven by diffusion, then the residence may be seen as an average residence time in the spot of cleavage light of a non-incorporated nucleotide. An optical arrangement may further be configured to provide the irradiated cleavage light with an intensity such that $t_{cleavage}$ is smaller than $t_{residence}$. Consequently, no degradation of free and unbound nucleotides due to an undesired cleavage reaction happens. Thus, by configuring the device such that $t_{cleavage}$ is smaller than $t_{residence}$ the probability that a non-incorporated nucleotide is affected by cleaving is reduced or eliminated. In other words, to avoid cleavage reactions in the bulk the average residence time of the molecules in the evanescent field of the wiregrid should be smaller or much smaller than the reaction time required for cleavage at the pertinent intensity. With a depth of the evanescent field of the order of 25 nm or less and a diffusion coefficient of the nucleotide of the order of 1e–10 m$^2$/s the time it takes for the molecule to diffuse in and out the evanescent field can be estimated as: (5e–8 m)2/1e–10=25 µs. Depending on the illumination time required for unblocking the bound molecules the probability of damage can be derived. Assume an illumination time of 0.1 s this would be 1:4000, with an illumination time of 10 ms it would be 1:400, etc.

Likewise the total damage is proportional to the volume fraction in the evanescent field over the total volume of reagent solution. With a chamber height of 100 µm the ratio is 1:4000. This means that in the worst case of damaging all molecules in the evanescent field only 0.025% of the molecules will be damaged. With a read length of 100 finally 2.5% of the molecules in solution would be damaged (worst case) which is still acceptable from a sequencing point of view.

The above considerations are valid for a stationary fluid in the reaction chamber 149. If the reagent fluid is however circulated in the reaction chamber (as explained in more detail below), movement of the molecules is dominated by active pumping rather than by diffusion. To effect cooling by fluid circulation, it is desirable to change the fluid in the excitation volume repeatedly, for example between 10 and 100 times per interval between the start of two pulses of cleavage light. Under these circumstances the balance between the cooling effect one would like to achieve and not cleaving too many unbound nucleotides has to be considered (as cleaved unbound nucleotides incorporated into the DNA cannot be detected because they no longer have a fluorophore identifying the base). In particular, the residence time of the liquid in the excitation volume should be shorter than the UV cleavage time as otherwise no additional cooling is achieved (during UV cleavage).

If the volume which is excited by the cleavage light is assumed to be a cylinder with a diameter of about 100 nm and a height of about 25 nm, a very small volume of about $2\times10^{-8}$ µl or 0.02 pl results (in comparison to a total volume of the solution of typically about 1-5 ml). Hence one has to consider the concentration of the labeled nucleotides and the refresh rate, which could become between about 2 to 10 times replacing the volume, possibly between about 2 to 5 times. So in practice for a 5× replacement on a total of 10 ml solution, there is a factor of $10^{+11}$ between the volume irradiated with UV blocking light and the total volume per spot.

In the following, information for using the device of FIG. 1 (and FIG. 2) is provided. For an improved synchronization the unblocking step should be carried out as fast as possible, i.e. with the highest intensity possible. This can be achieved by focusing the UV-light with a lens and scanning the surface by moving the lens or the substrate. The unblocking step is carried out after reading the sequencing step. This reading can be carried out by scanning a focused beam or step-and-scan with field illumination. In a preferred embodiment the read scanning can be coupled to the unblocking scanning by integrating both light beams in a single actuator, possibly even in a single lens by aligning the light beams. Alternatively, two lenses can be integrated in a single stage or two separate stages can operate synchronously. This can also be implemented in the step and scan read approach, in which the UV-step is also carried out in a step and scan mode by illuminating the same field as the reader. The preferred embodiment will depend on the available UV light source and its power. One can also envision a single flash of UV for the total surface if enough power is available and/or the area of the sequencing surface is limited. In view of the reaction rate for the base incorporation for the sequencing reaction the local UV illumination time should be well below 1 minute.

A single fluid sequencing using a wiregrid as well as single molecule sequencing has been described above. The approaches may use so called 3'-unblocked reversible terminators in which a flash of UV light is needed to de-block the nucleotide so that the next labeled nucleotide with a fluorophore attached can be incorporated by the polymerase. Reading out the color of the incorporated nucleotide allows the base incorporated to be determined and hence sequencing to be done.

In the described procedures high intensity UV light is needed. Typical intensity values range from about 4 mW/cm$^2$ to about 1 W/cm$^2$. This corresponds to a considerable amount of energy that may cause heating in the wiregrid and the buffers containing the reagents.

In order to improve the system performance and avoid overheating of the wiregrid/local liquids and even of the cartridge, it is proposed to circulate the reagent liquid (here the buffer and the required enzymes/nucleotides) by pumping them, for instance by using a pneumatically driven pumping of the liquid of a pneumatically operated cartridge design. This will produce a cooling effect and help to avoid local overheating.

The aforementioned proposal is realized in the device 100 of FIG. 1 by a "circulation arrangement" 150 which is schematically indicated as a channel 151 connecting opposite ends of the reaction chamber 149. In the illustrated embodiment, the channel 151 comprises a pumping element 152 by which the fluid in the channel 151 can actively and controllably be pumped (in the direction shown be the arrow). This induces a forced circulation in the reaction chamber 149 with a flow of the reagent fluid along the surface 103. Thus the molecules 102 are always surrounded by the chemicals they need while excess heat, particularly heat generated by cleavage light, is carried away from the surface to avoid overheating.

The aforementioned excess heat will typically be released to the environment by the reagent fluid during its circulation through other components of the cartridge. In order to assist this process, a cooling element 153 acting as a heat sink may be provided. This may for example be an area or region with close thermal contact to the environment to allow for a cooling effect by the ambient atmosphere. Additionally or alternatively, the cooling element 153 may comprise some active cooling unit such as a Peltier element.

In a preferred embodiment, the (active, controlled) circulation of reagent fluid by the circulation arrangement 150 may be synchronized with the generation of heat at the surface 103, particularly with the irradiation of cleavage light 112. The active circulation may for example be limited to the intervals of UV de-blocking pulses.

Accordingly a sequencing system is provided in which sequencing is done using a wiregrid in combination with circulating the buffers containing the reagents to avoid overheating the system while de-blocking using UV light.

Figure 2:
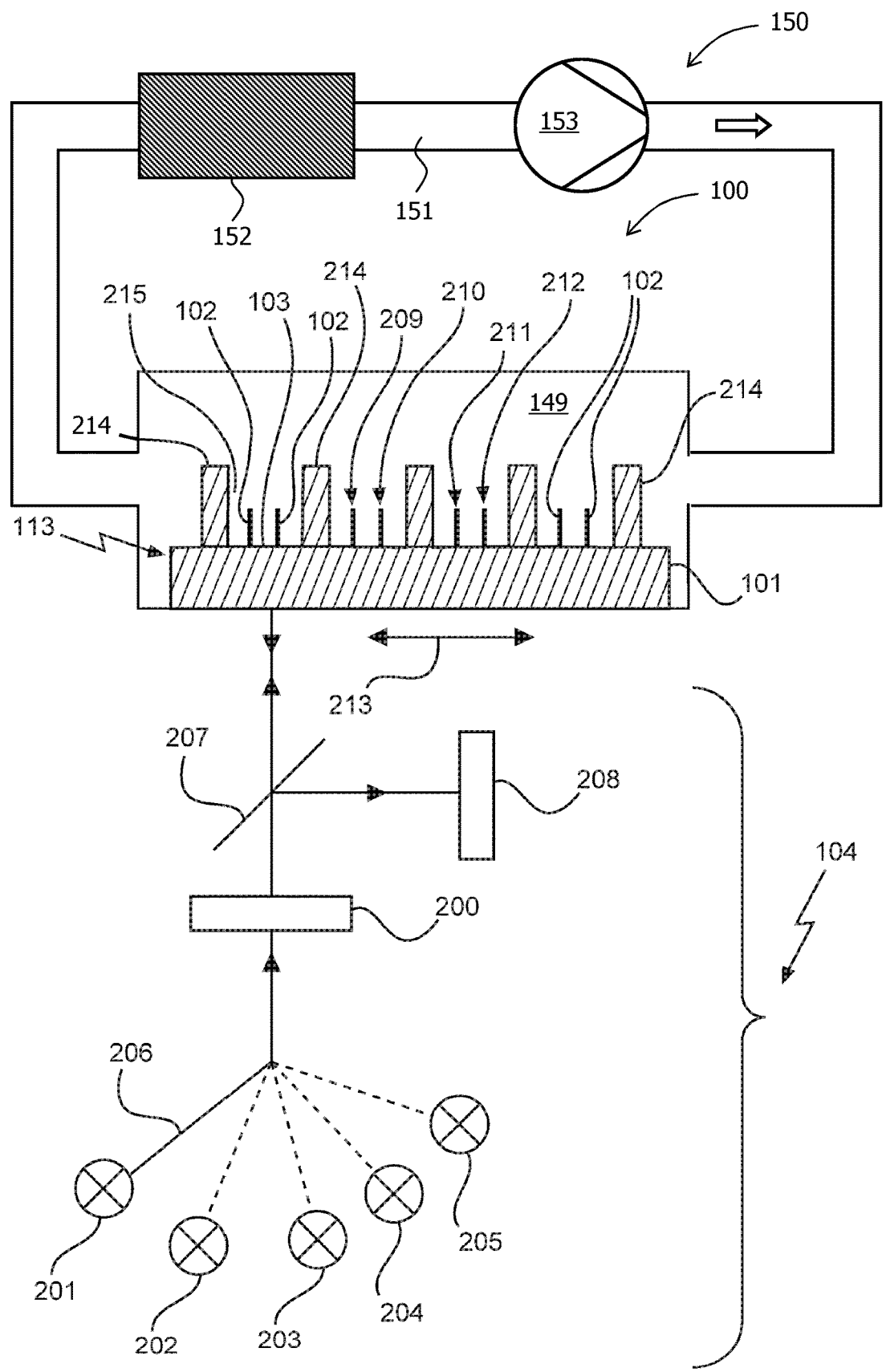
FIG. 2 schematically shows a second device according to an exemplary embodiment of the invention.

FIG. 2 shows a device 100 which is configured to optically control an iterative stepwise reaction to determine a sequence of a nucleic acid by synthesis. Similar to FIG. 1, a wiregrid substrate 113 is shown on which a plurality of molecules 102 are immobilized, i.e. are bound. As can be seen from FIG. 2, a regular pattern 214 provides for slit-like openings 215 in which the molecules 202 are bound on the first surface 103. The substrate comprises several adjacent binding positions 209, 210, 211 and 212 for binding molecules to the first surface along a first direction 213. Said binding positions may be seen as spots which can be covered with clones of identical molecules, such that the optical signal, which is generated, can be increased. The substrate 101 then provides for an array of such spots, i.e. of such binding positions, with respectively different clones. This may enhance the throughput. Both devices 100 of FIGS. 1 and 2 allow a nucleic acid sequencing with only one liquid, thereby avoiding the need to provide for washing steps in which the solution liquid is changed.

Furthermore, the optical arrangement 104 comprises five different light sources 201 to 205. The light sources 201 to 204 may be seen as excitation light sources in order to provide for four different excitation wavelength $\lambda_{Ex1}$ to $\lambda_{Ex4}$ as described previously. The light source 205 provides for cleavage light with a wavelength $\lambda_{CL}$. For example, the light source 205 may emit UV light. Reference numeral 206 symbolically depicts a switching device which allows the optical arrangement 104 to switch between the five wavelengths $\lambda_{Ex1}$ to $\lambda_{Ex4}$ and $\lambda_{CL}$. Furthermore, the light emitted by at least one of said light sources 201 to 205 is directed towards the polarization filter 200. Furthermore, a dichroic mirror 207 is shown which transmits the emitted light of the light sources 201 to 205 towards the substrate 101. After a fluorescent label has been excited by an evanescent wave of excitation light (at least one of the wavelengths $\lambda_{Ex1}$ to $\lambda_{Ex4}$), the fluorescence photons emitted by the fluorescent label or labels are directed towards the dichroic mirror 207 and are directed towards fluorescence detector 208. As can be seen from FIG. 2, the optical arrangement 104 may be scanned along the direction 213. Consequently, the device 100 of FIG. 2 is configured to perform an optical scan by moving the substrate 101 and the optical arrangement 104 relative to each other along the first direction 213. Consequently, the device allows to perform the optical scan such that each binding position is firstly irradiated with the excitation light and subsequently and secondly is irradiated the cleavage light of the cleavage wavelength in a movement along the first direction 213. The unblocking step, using the cleavage light, can thus be carried out after reading the fluorescence of the excited incorporated nucleotides.

FIG. 2 further indicates a circulation arrangement 150 as described above with respect to FIG. 1 which allows for a controlled circulation of reagent fluid through the reaction chamber 149 and along the reaction surface with the molecules 102, 209, 210, 211, 212. It should be noted that the flow of reagent fluid may in general have any orientation with respect to the wiregrid 113. It may for example be parallel to the direction 213, as shown, or perpendicular or have any other orientation that is convenient in the case at hand.

Further details and other exemplary devices and methods may be found in the WO 2013/105025 A1 which is entirely incorporated into the present text by reference.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A device for optically controlling a chemical reaction in a reaction chamber comprising a reagent fluid, said device comprising:
   a substrate for binding at least one molecule on a first surface of the substrate, wherein said first surface is a wall of the reaction chamber and wherein the substrate is configured as a wiregrid;
   an optical arrangement configured to direct cleavage light to the substrate to optically induce a photochemical cleavage reaction;

a circulation arrangement for circulating the reagent fluid in the reaction chamber, wherein the circulation arrangement comprises a channel connected with opposite ends of the reaction chamber and a pump configured to circulate the reagent fluid from the reaction chamber through the channel, and back into and through the reaction chamber, wherein the controller is configured to control the circulation such that a residence time of the reagent fluid in a volume excited by the cleavage light is shorter than a time the cleavage light is directed to optically induce the photochemical cleavage reaction; and wherein the circulation arrangement is configured to synchronize the circulation of the reagent fluid with the irradiation of cleavage light.

2. The device according to claim 1,
wherein the reagent fluid is circulated repeatedly along the first surface of the substrate.

3. The device according to claim 1,
wherein the circulation arrangement comprises at least one pneumatically driven actuator.

4. A method for optically controlling a chemical reaction in a reaction chamber comprising a reagent fluid, said method comprising:
providing a substrate with a molecule bound on a first surface of the substrate, wherein said first surface is a wall of the reaction chamber,
irradiating the substrate with cleavage light of a cleavage wavelength $\lambda_{CL}$, preferably UV light, by an optical arrangement and thereby optically inducing a photochemical cleaving reaction,
circulating the reagent fluid from the reaction chamber through a channel, back to the reaction chamber, and along the first surface, and
controlling the circulating based on a temperature of the reagent fluid.

5. The method according to claim 4, wherein the circulation is controlled such that a residence time of the reagent fluid in a volume excited by the cleavage light is shorter than a time the cleavage light is directed to optically induce the photochemical cleavage reaction.

6. The method according to claim 4,
wherein the circulation of the reagent fluid is synchronized with the irradiation of cleavage light.

7. The method according to claim 4, wherein the intensity of the cleavage light is larger than about 0.1 mW/cm$^2$.

8. The method according to claim 4, further comprising the steps:
irradiating the substrate with excitation light of at least a first excitation wavelength $\lambda_{Ex1}$ by an optical arrangement and thereby optically exciting a fluorescent label of a first nucleotide which is incorporated in the bound molecule on the substrate,
confining the excitation light by the substrate thereby providing for an evanescent wave of the excitation light by the substrate at the first surface of the substrate,
receiving and detecting fluorescence of the excited fluorescent label of the first incorporated nucleotide by the optical arrangement,
irradiating the substrate with the cleavage light and thereby optically inducing a photochemical cleaving reaction at the first incorporated nucleotide, and
confining the cleavage light of the cleavage wavelength $\lambda_{CL}$ by the substrate thereby providing for an evanescent wave of the cleavage light by the substrate at the first surface of the substrate.

9. A device for optically controlling a chemical reaction in a reaction chamber including a reagent fluid, said device comprising:
a substrate for binding at least one molecule on a first surface of the substrate, wherein said first surface is a wall of the reaction chamber;
an optical arrangement configured to direct cleavage light to the substrate to optically induce a photochemical cleavage reaction;
a channel connecting opposite ends of the reaction chamber and a pump configured to actively circulate the reagent fluid through the channel and the reaction chamber; and
a controller configured to control the pump based on a sensed temperature of the reagent fluid.

10. The device according to claim 9,
wherein the chemical reaction comprises a nucleic acid sequencing including an iterative stepwise reaction to determine a sequence of a nucleic acid by synthesis.

11. The device according to claim 9,
wherein the optical arrangement is configured to direct excitation light of at least a first excitation wavelength $\lambda_{Ex1}$ to the substrate to excite a fluorescent label of a first nucleotide incorporated into the molecule bound on the first surface of the substrate,
wherein the optical arrangement is further configured to receive and detect fluorescent light emitted by the fluorescent label of the first nucleotide incorporated into the bound molecule.

12. The device according to claim 11,
wherein the cleavage light has a cleavage wavelength $\lambda_{CL}$ to optically induce a photochemical cleavage reaction at the first incorporated nucleotide to cleave a blocking moiety and the fluorescent label away from the first incorporated nucleotide.

13. The device according to claim 12, the device further comprising:
the molecule which is bound to the first surface of the substrate,
a solution with a plurality of nucleotides and an enzyme, wherein the nucleotides respectively comprise the blocking moiety,
wherein the blocking moiety is configured to block a synthesizing activity of the enzyme when the respective nucleotide is incorporated into the molecule bound to the first surface.

14. The device according to claim 9,
wherein the substrate is configured to confine the excitation light and is configured to provide for an evanescent wave of the excitation light at the first surface of the substrate, and/or
wherein the substrate is configured to confine the cleavage light and is configured to provide for an evanescent wave of cleavage light at the first surface of the substrate.

15. The device according to claim 9, wherein the channel is connected with opposite first and second ends of the reaction chamber on opposite sides of the substrate, the channel being configured to circulate the reagent fluid from the first end of the reaction chamber, through the channel, back into the agent chamber at the second end, along the first surface, and back to the first end of the reaction chamber.

16. A device for optically controlling a chemical reaction of a reagent fluid in a reaction chamber, said device comprising:

a substrate configured to bind at least one molecule on a first surface of the substrate, wherein said first surface is a wall of the reaction chamber;

an optical arrangement configured to direct cleavage light to the substrate to optically induce a photochemical cleavage reaction;

a channel connected with opposite ends of the reaction chamber;

a pump configured to circulate the reagent fluid from the reaction chamber through the channel, and back into and through the reaction chamber; and a controller configured to control the optical arrangement and the pump to synchronize circulating the reagent fluid with delivery of the cleavage light such that a residence time of the reagent fluid in a volume excited by the delivered cleavage light is shorter than a time the cleavage light is directed to optically induce the photochemical cleavage reaction.

17. The device according to claim 16, wherein the controller is configured to control the optical arrangement such that circulating the reagent fluid in the reaction chamber takes place simultaneously with directing the cleavage light to the substrate.

18. A method for optically controlling a chemical reaction in a reaction chamber comprising a reagent fluid, said method comprising:

providing a substrate with a molecule bound on a first surface of the substrate, wherein said first surface is a wall of the reaction chamber, irradiating the substrate with cleavage light of a cleavage wavelength $\lambda_{CL}$ by an optical arrangement and thereby optically inducing a photochemical cleaving reaction, circulating the reagent fluid from the reaction chamber through a channel, back to the reaction chamber, and along the first surface, such that a residence time of the reagent fluid in a volume excited by the cleavage light is shorter than a time the cleavage light is directed to optically induce the photochemical cleavage reaction.

19. The method according to claim 18, further including: controlling the optical arrangement and pump to synchronize circulating the reagent fluid with delivery of the cleavage light such that circulating the reagent fluid in the reaction chamber takes place simultaneously with directing the cleavage light to the substrate.

* * * * *